US012805703B2

(12) United States Patent
Cowden

(10) Patent No.: US 12,805,703 B2
(45) Date of Patent: Nov. 24, 2026

(54) MULTI-ENDOSCOPE PLATFORM COUPLING

(71) Applicant: Boston Scientific Scimed, Inc., Maple Grove, MN (US)

(72) Inventor: Corbin Cowden, Houston, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 246 days.

(21) Appl. No.: 18/526,428

(22) Filed: Dec. 1, 2023

(65) Prior Publication Data

US 2024/0180401 A1 Jun. 6, 2024

Related U.S. Application Data

(60) Provisional application No. 63/429,337, filed on Dec. 1, 2022.

(51) Int. Cl.
*A61B 1/00* (2006.01)

(52) U.S. Cl.
CPC ...... *A61B 1/00128* (2013.01); *A61B 1/00119* (2013.01); *A61B 1/0014* (2013.01)

(58) Field of Classification Search
CPC ............ A61B 1/00119; A61B 1/00128; A61B 1/0014; A61B 1/00121; A61B 1/00137; A61B 2017/00477; A61B 2018/00172; A61B 1/00019; A61M 39/10; A61M 2039/1033; A61M 2039/1038; A61M 2039/1077; F16L 37/2445; F16L 37/248; F16L 37/252; F16L 15/08; F16L 33/24
See application file for complete search history.

(56) References Cited

U.S. PATENT DOCUMENTS

| | | | | |
|---|---|---|---|---|
| 5,234,417 A * | 8/1993 | Parks | .................. | A61J 15/0026 604/905 |
| 5,447,343 A | 9/1995 | Gajewski et al. | | |
| 6,168,213 B1 * | 1/2001 | Muller | .................. | E21B 43/116 285/391 |
| 6,250,688 B1 * | 6/2001 | Kirby | .................... | F16L 37/113 285/360 |

(Continued)

FOREIGN PATENT DOCUMENTS

JP 2002017871 A 1/2022

OTHER PUBLICATIONS

International Search Report and Written Opinion for International Application No. PCT/US2023/082028, dated Feb. 15, 2024. (13 pages).

*Primary Examiner* — Aaron B Fairchild
(74) *Attorney, Agent, or Firm* — Seager, Tufte & Wickhem, LLP

(57) ABSTRACT

Connectors arranged and configured to couple a tube set to an endoscope. An illustrative connector may comprise a housing having a generally tubular body, the housing including a first end, a second end, and a lumen extending therethrough, a first coupling mechanism adjacent to the first end of the housing, and a second coupling mechanism extending from a first end adjacent to the first end of the housing to a second end, the second end of the second coupling mechanism positioned between the first end and the second end of the housing. The second coupling mechanism may be different from the first coupling mechanism.

15 Claims, 9 Drawing Sheets

(56) References Cited

U.S. PATENT DOCUMENTS

| | | | | |
|---|---|---|---|---|
| 6,283,511 | B1 * | 9/2001 | Kamp | F16L 37/2445 285/391 |
| 8,529,439 | B2 | 9/2013 | Ito et al. | |
| 8,764,642 | B2 | 7/2014 | Bendele et al. | |
| 9,560,953 | B2 | 2/2017 | Gilreath et al. | |
| 9,560,954 | B2 | 2/2017 | Jacobs et al. | |
| 2005/0245899 | A1 | 11/2005 | Swisher | |
| 2008/0073911 | A1 * | 3/2008 | Wells | F16L 15/008 285/369 |
| 2020/0096142 | A1 | 3/2020 | Greep et al. | |
| 2022/0095906 | A1 | 3/2022 | Stanton et al. | |

* cited by examiner

MULTI-ENDOSCOPE PLATFORM COUPLING

CROSS-REFERENCE TO RELATED APPLICATIONS

This application claims the benefit of U.S. Provisional Patent Application Ser. No. 63/429,337 filed on Dec. 1, 2022, the disclosure of which is incorporated herein by reference.

FIELD

This disclosure relates generally to medical device coupling assemblies and methods, and particularly to coupling mechanisms to supply fluid and/or gas to an endoscope.

BACKGROUND

Conventionally, endoscope devices have been widely used for performing diagnostic and/or therapeutic treatments. Endoscope devices are often coupled to additional devices, such as, but not limited to, processors, light sources, water sources, gas sources, etc. For example, water is supplied to the endoscope for irrigation and lens washing while air/gas is supplied for insufflation of the working lumen. As new endoscope technologies emerge, the new technologies may not be backwards compatible with older technology. Further, different brands of endoscopes may incorporate different connection types. This may necessitate more than one connector or types of connector be available for coupling the additional devices to the endoscope. However, having multiple pieces of tubing, hoses, couplers, etc. can be cumbersome within the procedure suite.

It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a connector arranged and configured to couple a tube set to an endoscope may comprise a housing having a generally tubular body, the housing including a first end, a second end, and a lumen extending therethrough, a first coupling mechanism adjacent to the first end of the housing, and a second coupling mechanism extending from a first end of the second coupling mechanism adjacent to the first end of the housing to a second end of the second coupling mechanism, the second end of the second coupling mechanism positioned between the first end and the second end of the housing. The second coupling mechanism may be different from the first coupling mechanism.

Alternatively or additionally to any of the examples above, in another example, the connector may further comprise a third coupling mechanism positioned between the second end of the second coupling mechanism and the second end of the housing, the third coupling mechanism may be different from the first and the second coupling mechanisms.

Alternatively or additionally to any of the examples above, in another example, the first coupling mechanism may comprise external threading extending about an outer surface of the tubular body.

Alternatively or additionally to any of the examples above, in another example, the external threading may be discontinuous about a circumference of the generally tubular body.

Alternatively or additionally to any of the examples above, in another example, the first coupling mechanism may comprise a first segment and a second segment, the first and second segments may each have an arc length of less than 180° and may be separated by a first and a second cut-out region.

Alternatively or additionally to any of the examples above, in another example, the first and second segments may include threading extending about an outer surface thereof.

Alternatively or additionally to any of the examples above, in another example, the second coupling mechanism may comprise a first helically extending recess and a second helically extending recess formed in an inner surface of the generally tubular body, the first and second helically extending recesses may be spatially separated from one another.

Alternatively or additionally to any of the examples above, in another example, each of the first and second helically extending recesses may extend less than 1800 about an inner circumference of the generally tubular body.

Alternatively or additionally to any of the examples above, in another example, each of the first and second helically extending recesses may extend from a first end to a second end.

Alternatively or additionally to any of the examples above, in another example, the connector may further comprise a mechanical stop positioned adjacent to the second end of each of the first and second helically extending recesses.

Alternatively or additionally to any of the examples above, in another example, the third coupling mechanism may comprise an internal thread extending about an inner surface of the generally tubular body.

Alternatively or additionally to any of the examples above, in another example, the internal thread may be formed about the inner surface of a radially inward extending annular ledge.

Alternatively or additionally to any of the examples above, in another example, the connector may further comprise a sealing member positioned adjacent to the first coupling mechanism.

Alternatively or additionally to any of the examples above, in another example, the connector may further comprise a sealing member positioned adjacent to the second coupling mechanism.

Alternatively or additionally to any of the examples above, in another example, the connector may further comprise a sealing member positioned adjacent to the third coupling mechanism.

In another example, a connector arranged and configured to couple a tube set to an endoscope may comprise a housing having a generally tubular body, the housing including a first end, a second end, and a lumen extending therethrough a first coupling mechanism adjacent to the first end of the housing, the first coupling mechanism comprising a first segment and a second segment, the first and second segments each having an arc length of less than 1800 and separated by a first cut-out region and a second cut-out region, and a second coupling mechanism, the second coupling mechanism comprising a first helically extending recess and a second helically extending recess formed in an inner surface of the generally tubular body, the first helically extending recess extending from a first end adjacent to the first cut-out region to a second end and the second helically extending recess extending from a first end adjacent to the second cut-out region to a second end. The first coupling mechanism may be configured to couple to a first receiver type and the second coupling mechanism may be configured to couple to a second receiver type, the second receiver type may be different from the first receiver type.

Alternatively or additionally to any of the examples above, in another example, the connector may further comprise a third coupling mechanism, the third coupling mechanism may comprise internal threading extending about an inner surface of the generally tubular body.

Alternatively or additionally to any of the examples above, in another example, the connector may further comprise at least one sealing member positioned adjacent to the first or second coupling mechanism.

Alternatively or additionally to any of the examples above, in another example, the first receiver type may comprise an internally threaded receiver and the second receiver type may comprise a female Luer-type receiver.

In another example, a connector arranged and configured to couple a tube set to an endoscope may comprise a housing having a generally tubular body, the housing including a first end, a second end, and a lumen extending therethrough, a radially inward extending ledge positioned between the first end and the second end of the housing within the lumen of the housing, a first coupling mechanism adjacent to the first end of the housing, the first coupling mechanism comprising a first segment and a second segment, the first and second segments each having an arc length of less than 1800 and separated by a first cut-out region and a second cut-out region, a second coupling mechanism, the second coupling mechanism comprising a first helically extending recess and a second helically extending recess formed in an inner surface of the generally tubular body, the first helically extending recess extending from a first end adjacent to the first cut-out region to a second end and the second helically extending recess extending from a first end adjacent to the second cut-out region to a second end, and a third coupling mechanism, the third coupling mechanism comprising internal threading extending about an inner surface of the radially inward extending ledge. The first coupling mechanism may be configured to couple to a first receiver type, the second coupling mechanism may be configured to couple to a second receiver type, and the third coupling mechanism may be configured to couple to a third receiver type, the second receiver type may be different from the first receiver type and the third receiver type may be different from both the first and the second receiver types.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
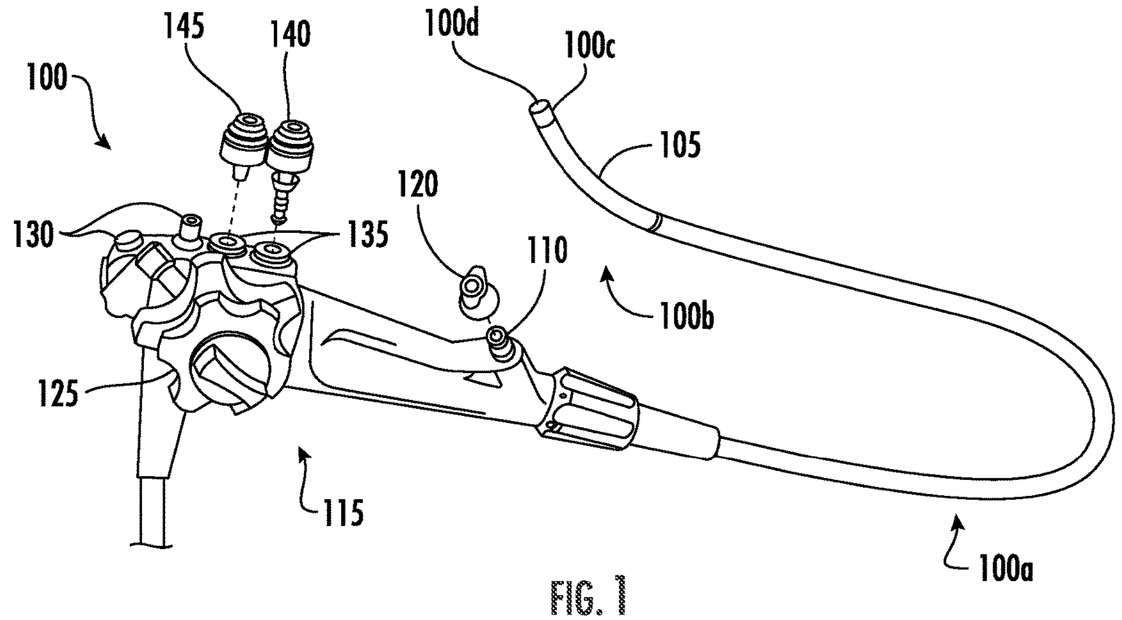
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Although embodiments of the present disclosure are described with specific reference to coupling a water and/or gas tubing to a connector portion of an endoscope, it should be appreciated that such embodiments may be used to couple various tubes in a variety of applications.

Although the present disclosure includes description of a bottle and tube set, couplers, connectors, and/or cap suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. Endoscope devices are often coupled to additional devices, such as, but not limited to, processors, light sources, water sources, gas sources, etc. For example, water is supplied to the endoscope for irrigation and lens washing while air/gas is supplied for insufflation of the working lumen. As new endoscope technologies emerge, the new technologies may not be backwards compatible with older technology. Further, each brand of endoscope may incorporate a different connection type for connecting tube sets to the endoscope. This may necessitate more than one connector or types of connector be available for coupling the additional devices to the endoscope. However, having multiple pieces of tubing, hoses, couplers, etc. can be cumbersome within the procedure suite. Disclosed herein are methods and systems for coupling fluid and gas lines across multiple endoscopic platforms with a single connector.

Figure 2:
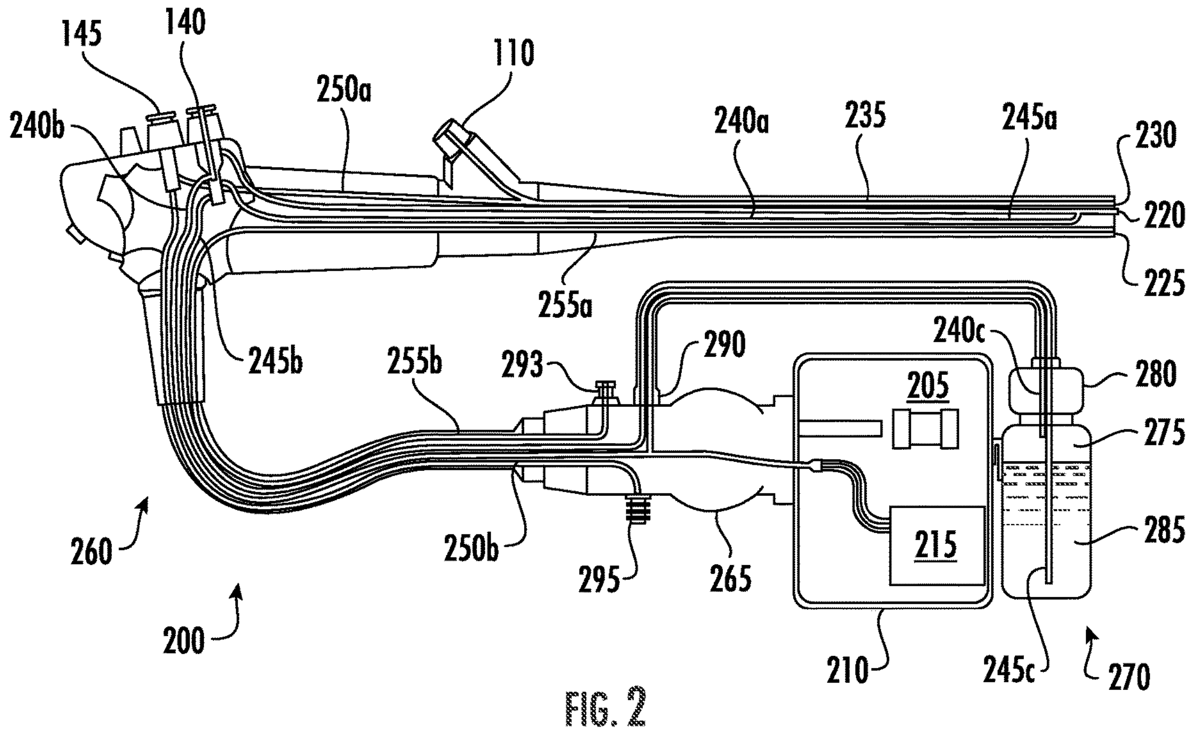
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245*c*, may be placed in the path of the irrigation supply tubing to help prevent back-flow into the reservoir after water has passed the valve. In some cases, irrigation water may be supplied from the water reservoir 270. Some illustrative systems where the supply tubing for irrigation and lens wash are connected to and drawn from a single water reservoir are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference.

In some cases, the type of receiver or coupling configuration of the gas/lens wash connection 290 for receiving the lens wash supply tube 245*c* on the outside of the connector portion 265 may vary depending on the manufacturer and/or age of the connector portion 265. While the illustrative connectors are described with respect to the lens wash tubing 245*c* and/or its respective receiver or coupler on the connector portion 265, it should be understood the receivers and coupling configurations described herein may be used at other connection points, as desired.

Figure 3:
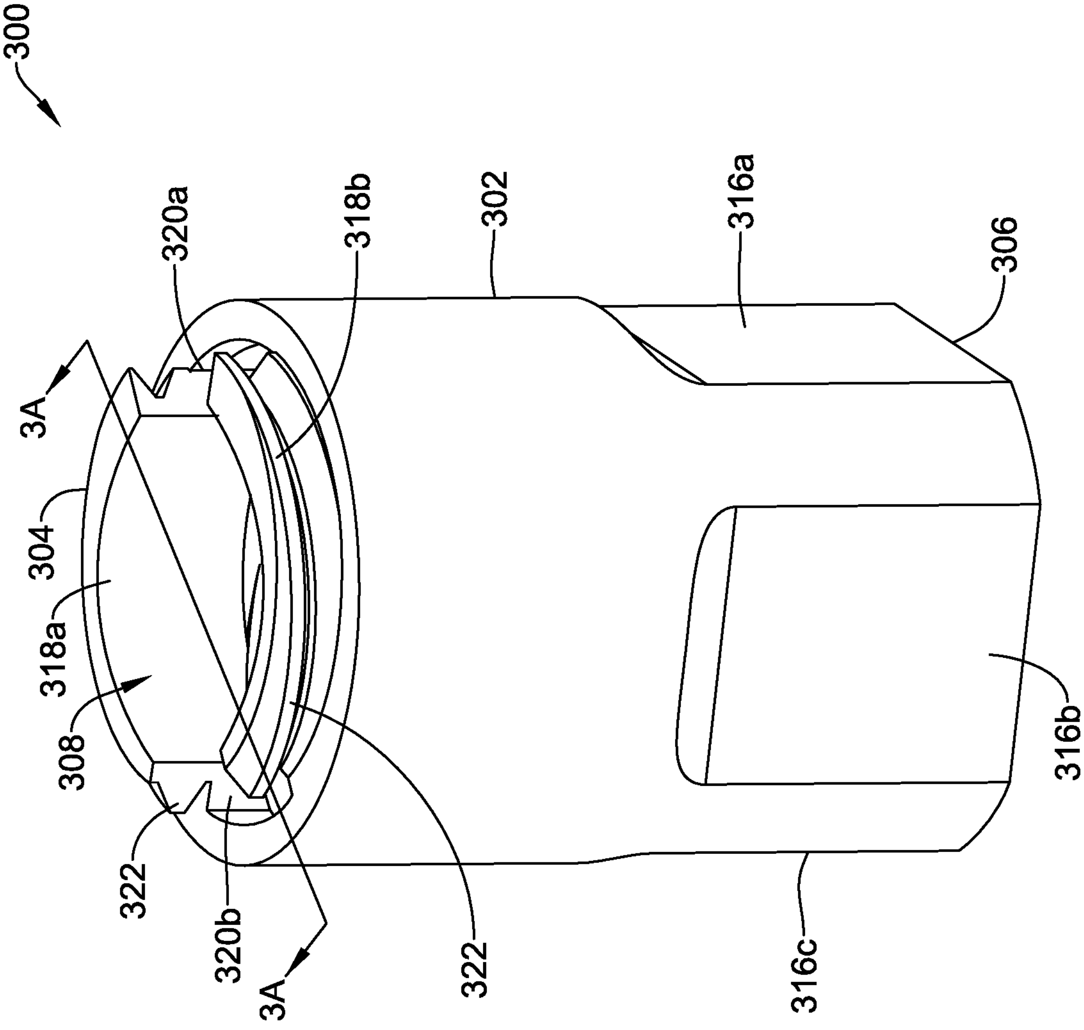
FIG. 3 depicts a perspective view of an illustrative connector.
Figure 3A:
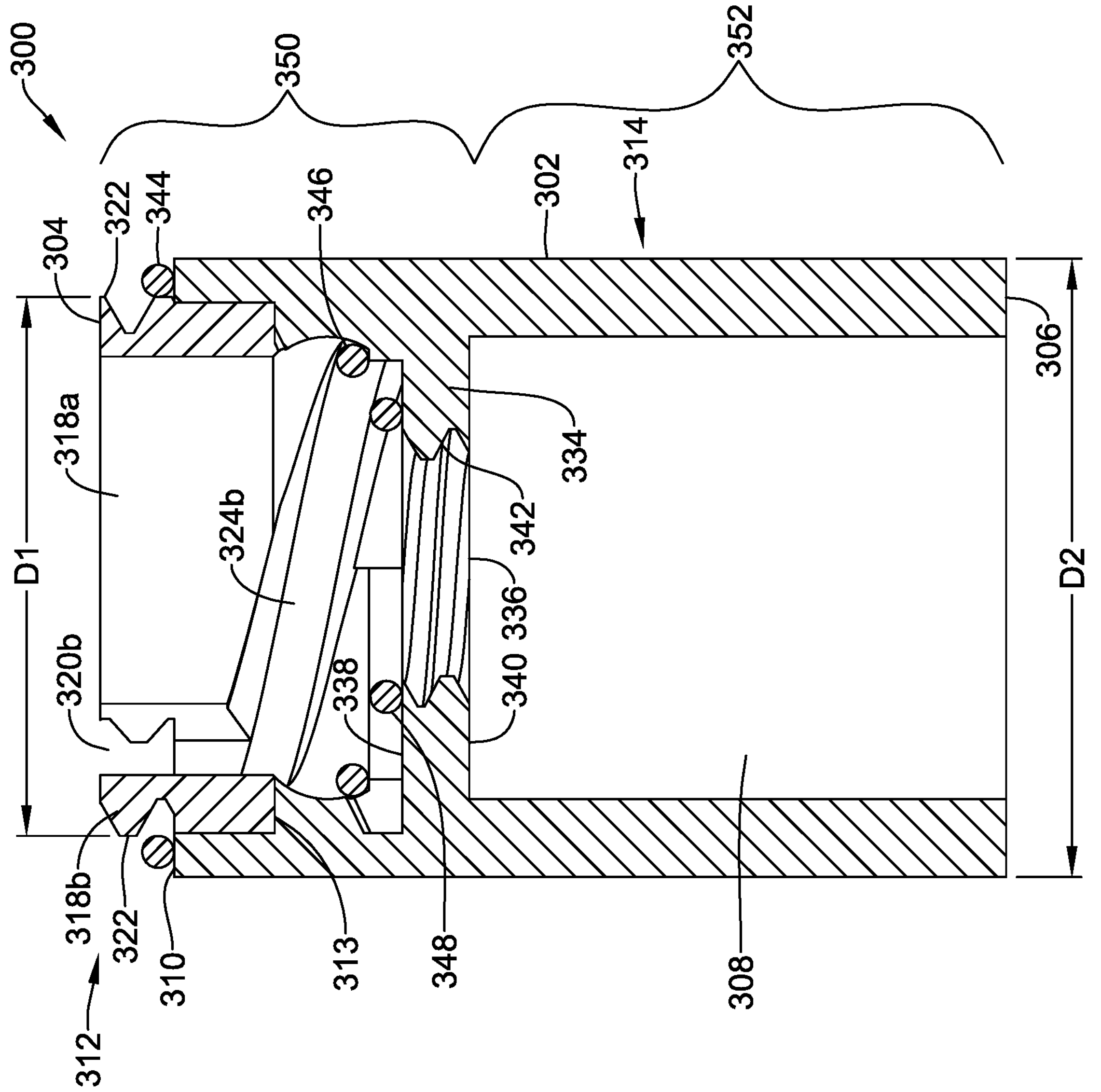
FIG. 3A depicts a cross-sectional view of the illustrative connector, taken at line 3A-3A of FIG. 3.
Figure 4:
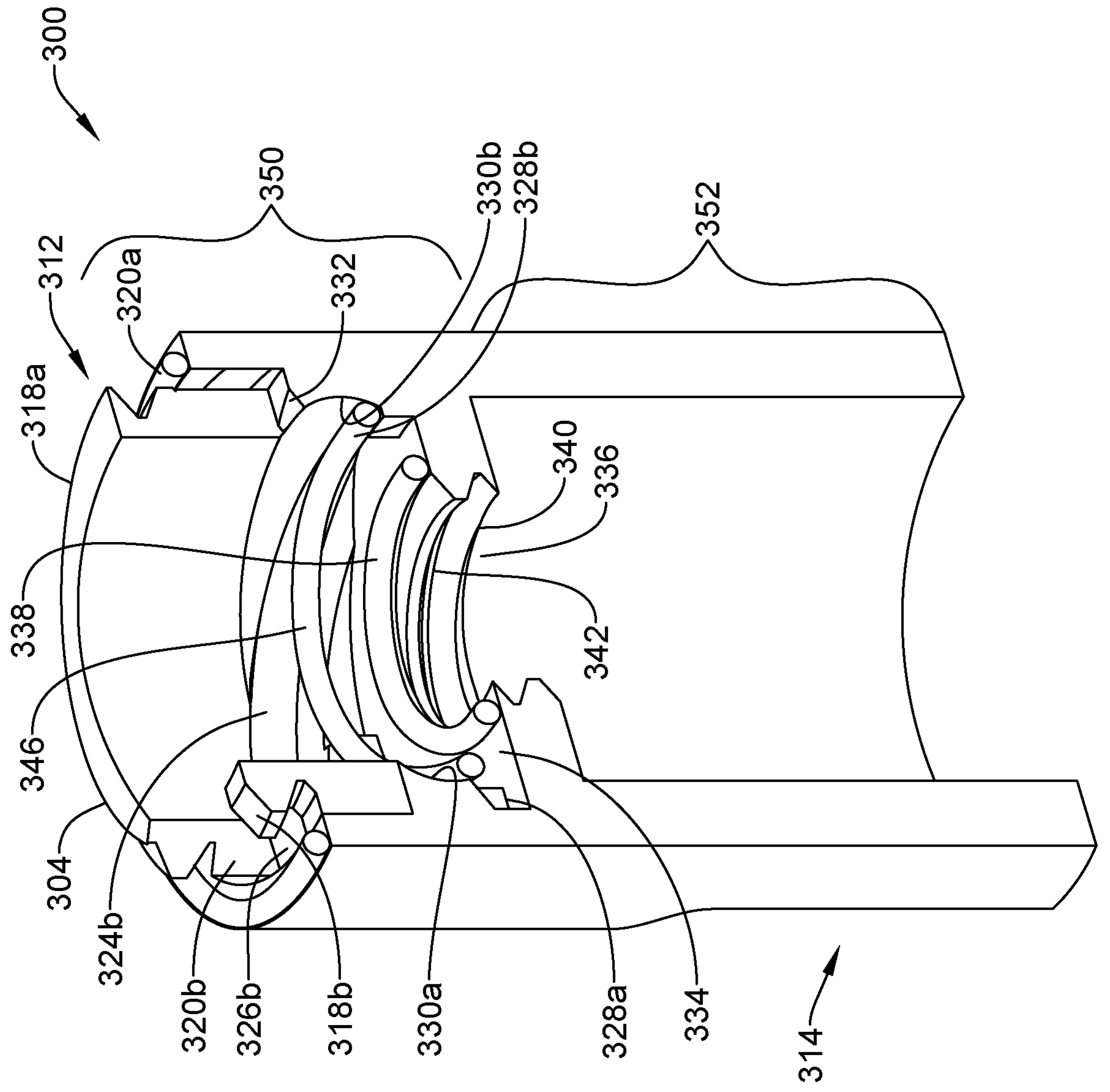
FIG. 4 depicts a partial cross-sectional view of the illustrative connector of FIG. 3.
Figure 5A:
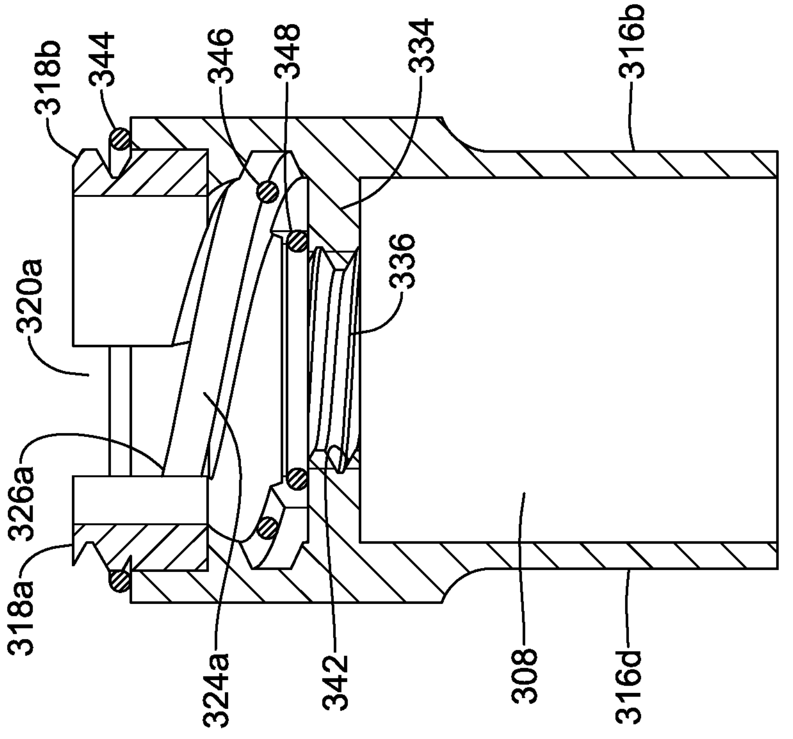
FIG. 5A depicts a cross-sectional view of the illustrative connector, taken at line 5A-5A of FIG. 5.
Figure 5:
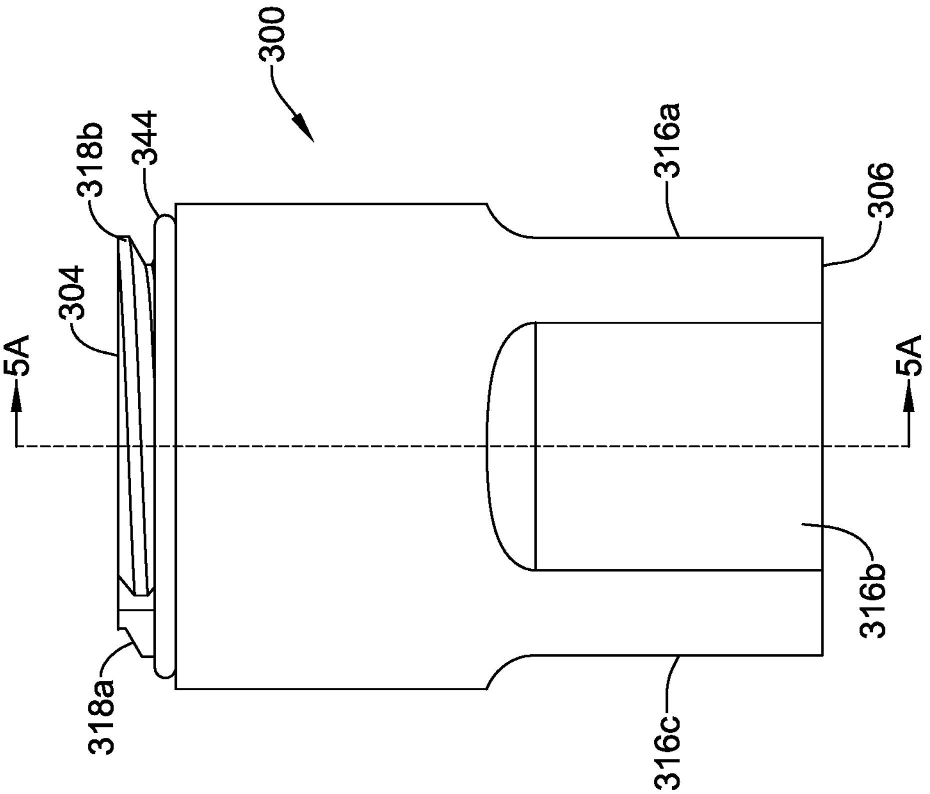
FIG. 5 depicts a first side view of the illustrative connector of FIG. 3.
Figure 6A:
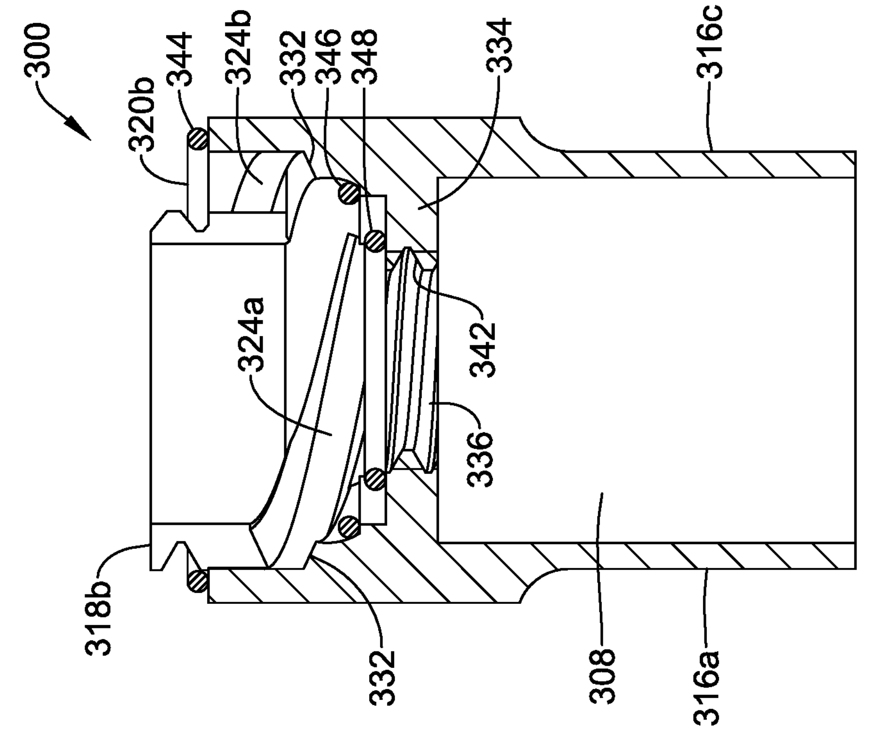
FIG. 6A depicts a cross-sectional view of the illustrative connector, taken at line 6A-6A of FIG. 6.
Figure 6:
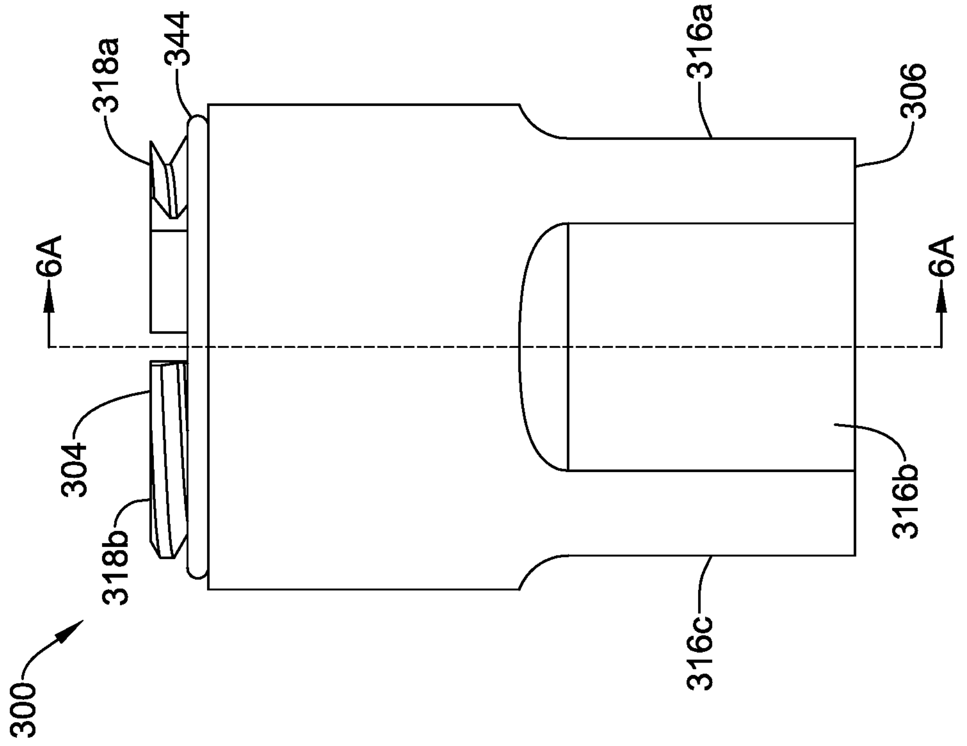
FIG. 6 depicts a second side view of the illustrative connector of FIG. 3.

FIG. 3 depicts a perspective view of an illustrative connector 300 that may be used to couple the lens wash tubing 245*c* to the connector portion 265. FIG. 3A depicts a cross-sectional view of the illustrative connector 300, taken at line 3A-3A of FIG. 3. FIG. 4 depicts a partial cross-sectional view of the illustrative connector 300. FIG. 5 depicts a first side view of the illustrative connector 300. FIG. 5A depicts a cross-sectional view of the illustrative connector 300, taken at line 5A-5A of FIG. 5. FIG. 6 depicts a second side view of the illustrative connector 300. FIG. 6A depicts a cross-sectional view of the illustrative connector 300, taken at line 6A-6A of FIG. 6. Generally, the connector 300 may include two or more coupling mechanisms configured to allow the connector 300 to be coupled to two or more different types of receivers or coupling mechanisms on (or coupled to) the connector portion 265. While the connector 300 is described with respect to the lens wash tubing 245*c*, it should be understood that the connector 300 may be used in other connection points through the endoscope 100 and system 200. In some cases, the connector 300 may be used to couple coaxially extending gas/lens wash tubing 240*c*, 245*c* to the connector portion 265.

The connector 300 may include a generally tubular body 302 extending from a first end 304 to a second end 306. Generally, the first end 304 may be configured to be coupled to the connector portion 265 of an umbilicus 260 while the second end 306 may be configured to be coupled to the lens wash tubing 245*c*. The body 302 may define a lumen 308 extending from the first end 304 to the second end 306. The lumen 308 may vary in diameter along a length thereof. Referring additionally to FIG. 3A, the body 302 may have a first outer diameter D1 adjacent to the first end 304 and a second outer diameter D2 adjacent to the second end 306. The second outer diameter D2 may be greater than the first outer diameter D1. In some embodiments, outflow check valves or other one-way valve configurations (not shown) may be placed in the lumen 308 of the connector 300 to help prevent water from back-flowing into the reservoir 270 after the water has passed the valve.

In some embodiments, the body 302 may be formed from a first portion 312 and a second portion 314. In some cases, the first and second portions 312, 314 may be formed from separate components that are subsequently assembled together (e.g., press-fit, adhesive bonded, ultrasonic welded, etc.). For example, the first portion 312 may have an outer diameter D1 that is smaller than an inner diameter of the second portion 314 adjacent the first end 310 thereof and the first portion 312 may be at least partially positioned within a lumen of the second portion 314. In some cases, the second end 313 of the first portion 312 may rest on a first radially inward extending ledge 332 of the second portion 314. The inwardly extending ledge 332 may transition the lumen 308 of the connector 300 from a first diameter adjacent the first end 310 thereof to a second smaller diameter. In other examples, the first and second portions 312, 314 may be formed as a single monolithic structure.

The first portion 312 may extend from the first end 304 of the connector 300 to a second end 313. The second portion 314 may extend from a first end 310 to the second end 306 of the connector 300. In some embodiments, the first end 310 of the second portion 314 may be located at a transition point between the first outer diameter D1 and the second outer diameter D2, although this is not required. The second end 313 of the first portion 312 may be positioned between the first end 310 of the second portion 314 and the second end 306 of the connector 300. However, this is not required. In some examples, the second end 313 of the first portion 312 may be positioned adjacent to or generally aligned with the first end 310 of the second portion 314.

The second portion 314 may have a generally cylindrical outer surface. In some embodiments, the second portion 314 may include one or more flattened regions 316*a*, 316*b*, 316*c*, 316*d* spaced about a circumference of the second portion 314 adjacent the second end 306. In some embodiments, the second portion 314 may include four flatted regions 316*a-d* uniformly spaced about the circumference of the second portion 314. However, this is not required. In some examples, the second portion 314 may include fewer than four or more than four flattened regions, if so desired. It is further contemplated that the flattened regions may be eccentrically positioned about the second portion 314. The flattened regions 316*a-d* may extend over less than an entire length of the second portion 314 or along an entire length thereof. In yet other examples, the flattened regions may be omitted entirely. It is contemplated that the flattened regions 316*a-d* may enhance the ability of the connector 300 to be securely gripped.

The first portion 312 may be at least partially discontinuous about a circumference thereof. For example, the first portion 312 may include a first segment 318*a* and a second segment 318*b* that collectively extend about less than 360°. The first and second segments 318*a*, 318*b* may be separated from one another by a first cut-out region 320*a* defining a first region free from material and a second cut-out region 320*b* defining a second region free from material. The first and second cut-out regions 320*a*, 320*b* may extend from the first end 304 of the connector 300 toward the second end 313 of the first portion 312. In some examples, the first and second cut out regions 320*a*, 320*b* may extend along an entire length of the first portion 312 (e.g., from the first end 304 of the connector to the second end 313 of the first portion 312). In other examples, the first and second cut-out regions 320*a*, 320*b* may extend along less than an entire length of the first portion 312. It is contemplated the first and second cut-out regions 320*a*, 320*b* may have a similar length to one another or may have differing lengths, as desired. Each of the first and second segments 318*a*, 318*b* may extend less than 180° about a circumference of the first portion 312. In the illustrated embodiments, the first and second segments 318*a*, 318*b* have a similar arc length. However, this is not required. It is contemplated that the arc length of the first and second segments 318*a*, 318*b* may depend at least in part on the arc length of the cut-out regions 320*a*, 320*b* which may be sized to receive the tabbed hub of a female Luer-type connection, as will be described in more detail herein.

Figure 7:
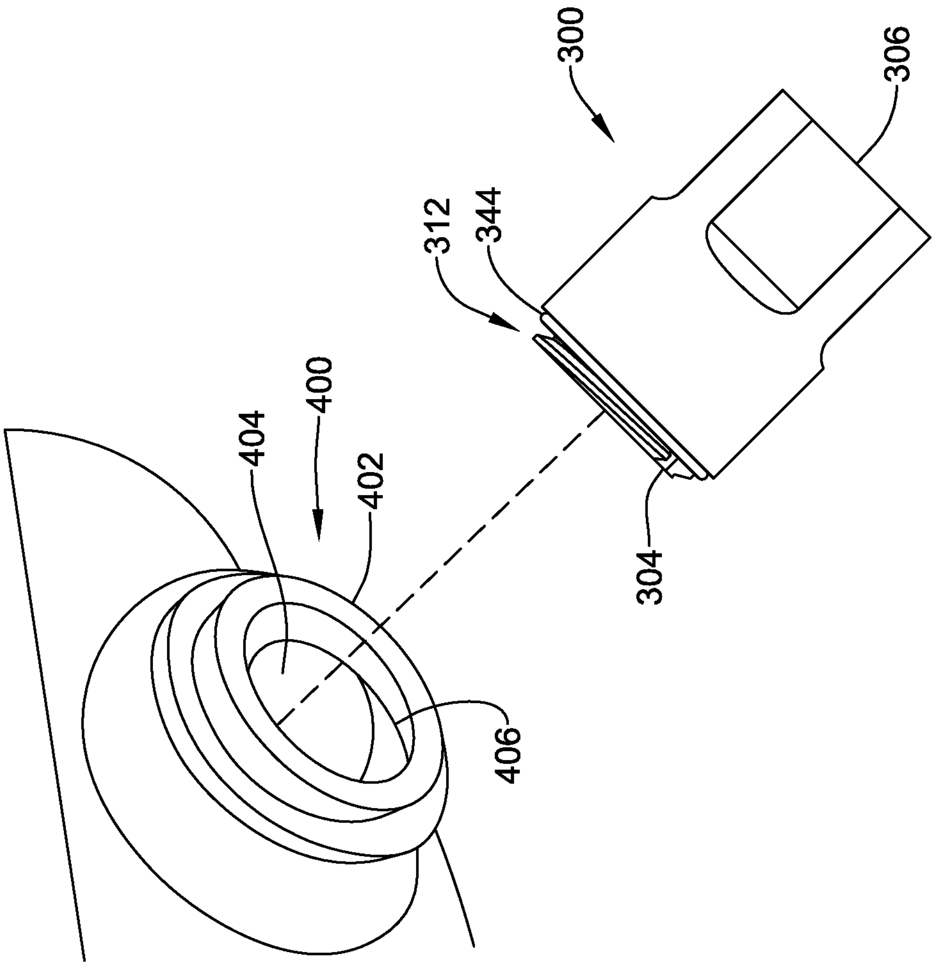
FIG. 7 depicts a perspective view of the illustrative connector of FIG. 3 with a first receiver of a first type.

The first and second segments 318*a*, 318*b* of the first portion 312 may define a first connection mechanism for coupling the connector 300 to a first type of receiver affixed to the connector portion 265. For example, the first and second segments 318*a*, 318*b* of the first portion 312 may include external (or male) threading 322 formed on an outer surface thereof. The external threading 322 may be configured to be coupled with mating internal (or female) threads of a receiver affixed to the connector portion 265. FIG. 7 depicts a perspective view of the illustrative connector 300 with a first receiver 400 of a first type. In the illustrated embodiment, the first receiver 400 may generally be an internally threaded receiver. The receiver 400 may have a generally tubular body 402 defining a lumen 404 extending therethrough. One or more internal threads 406 may be formed in the inner wall of the tubular body 402. The external threading 322 of the first portion 312 may be configured to engage the internal threading 406 of the first receiver 400. It is contemplated that the first portion 312 of the connector 300 may be inserted into the lumen 404 of the receiver 400. The external threading 322 of the connector 300 may be engaged with the internal threading 406 of the receiver 400 and the connector 300 rotated to secure the connector 300 to the receiver 400. The number of rotations required to secure the connector 300 to the receiver 400 may depend, at least in part, on a length of the first portion 312 and/or a number of threads present.

Returning to FIGS. 3A, 4, 5, 5A, 6, and 6A, the connector 300 may further include a first helically extending recess 324*a* and a second helically extending recess 324*b*. Collectively, the first and second helically extending recesses 324*a*, 324*b* may define a second coupling mechanism for coupling the connector 300 to a second type of receiver, different from the first type of receiver 400, affixed to the connector portion 265. The first helically extending recess 324*a* may extend from a first end 326*a* to a second end 328*a*. The first end 326*a* of the first helically extending recess 324*a* may be adjacent to the first cut-out region 320*a* such that a first tab of the tabbed hub of a female Luer-type connection may be inserted into the first cut-out region 320*a* and then into the first helically extending recess 324*a*. Adjacent to the second end 328*a* of the first helically extending recess 324*a* may be a side wall 330*a*. The side wall 330*a* may extend radially inward to provide a mechanical stop when the connector 300 is coupled with a second receiver type, as will be described in more detail herein. Similar to the first helically extending recess 324*a*, the second helically extending recess 324*b* may extend from a first end 326*b* to a second end 328*b*. The first end 326*b* of the second helically extending recess 324*b* may be adjacent to the second cut-out region 320*b* such that a second tab of the tabbed hub of a female Luer-type connection may be inserted into the second cut-out region 320*b* and into the second helically extending recess 324*b*. Adjacent to the second end 328*b* of the first helically extending recess 324*b* may be a side wall 330*b*. The side wall 330*b* may extend radially inward to provide a mechanical stop when the connector 300 is coupled with a second receiver type. The first and second helically extending recesses 324*a*, 324*b* may be spatially spaced from one another. For example, the first and second helically extending recesses 324*a*, 324*b* may be positioned about 180° from one another. However, other spacing arrangements may be used, as desired.

The first and second helically extending recesses 324*a*, 324*b* may be formed in an inner surface of the second portion 314 of the connector 300. For example, the first ends 326*a*, 326*b* of the first and second helically extending recesses 324*a*, 324*b* may be positioned adjacent to the second end 313 of the first portion 312. In some cases, the first and second helically extending recesses 324*a*, 324*b* may be formed at least partially in an inner surface of the first portion 312.

Figure 8:
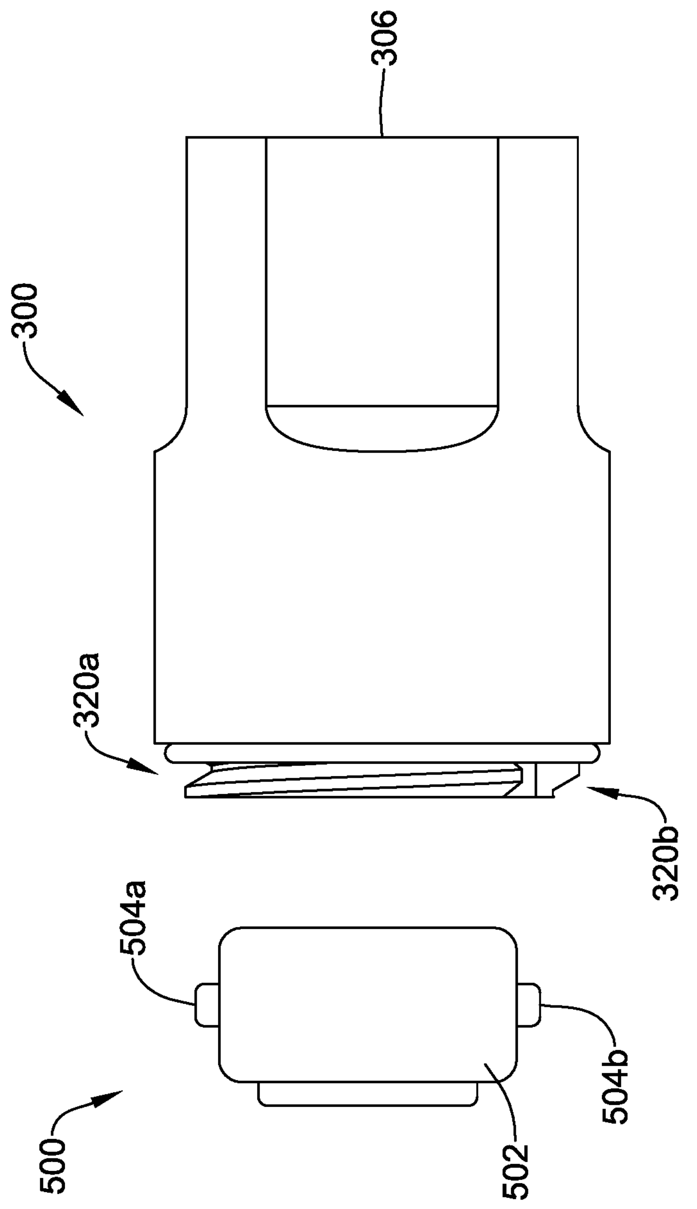
FIG. 8 depicts a side view of the illustrative connector of FIG. 3 with a second receiver of a second type.

FIG. 8 depicts a side view of the illustrative connector 300 with a second receiver 500 of a second type. The second receiver 500 may have a different connection mechanism from the first receiver 400. In the illustrated embodiment, the second receiver 500 may generally be a female Luer-type lock. The receiver 500 may have a generally tubular body 502 defining a lumen extending therethrough. The receiver 500 may include a first tab 504*a* extending radially from an outer surface of the tubular body 502. A second tab 504*b* may also extend radially from an outer surface of the tubular body 502. The first and second tabs 504*a*, 504*b* may be spaced approximately 180° from one another. However, this is not required. The tabs 504*a*, 504*b* may be spaced as desired. The tabs 504*a*, 504*b* may be configured to be inserted into the lumen 308 of the connector 300. For example, the tabs 504*a*, 504*b* may be aligned with the first and second cut-out regions 320*a*, 320*b* of the connector 300. It is contemplated that the first and second cut-out regions 320*a*, 320*b* may allow the tabs 504*a*, 504*b* to by-pass the first and second segments 318*a*, 318*b* and enter lumen 308. The connector 300 may be advanced along a longitudinal axis of the receiver 500 until the tabs 504*a*, 504*b* abut the inwardly extending ledge 332. The connector 300 may then be rotated to cause the first and second helically extending recesses 324*a*, 324*b* to move along the tabs 504*a*, 504*b* until the tabs 504*a*, 504*b* engage the side walls 330*a*, 330*b*. The number of rotations required to secure the connector 300 to the receiver 500 may depend, at least in part, on a number of turns of the first and second helically extending recesses 324*a*, 324*b*. For example, while each of the first and second helically extending recesses 324*a*, 324*b* are illustrated as extending about 180° about an inner circumference of the connector 300, the first and second helically extending recesses 324*a*, 324*b* may extend less than 180°, more than 180°, more than 270° or more than 360° about the inner circumference of the connector 300.

Returning to FIGS. 3A, 4, 5, 5A, 6, and 6A, the connector 300 may further include a second radially inward extending ledge 334 formed within the second portion 314 thereof. The second ledge 334 may divide the connector 300 into a first region 350 having a variable inner diameter defining a plurality of connection features for engaging a receiver and a second region 352 having a generally uniform inner diameter for engaging the lens wash tubing 245*c*. The second ledge 334 may be generally annular defining a through hole 336 extending through a thickness (e.g., from a first side 338 to a second 340) of the second ledge 334. The diameter of the lumen 308 of the connector 300 may be reduced at the through hole 336 relative to the diameter of the lumen 308 adjacent the first and/or second ends 304, 306 of the connector 300. A plurality of internal (or female) threads 342 may be formed in the inner surface of the second ledge 334. The internal threads 342 may define a third connection mechanism for coupling the connector 300 to a third type of receiver, different from both the first and second types of receivers 400, 500, affixed to the connector portion 265.

Figure 9:
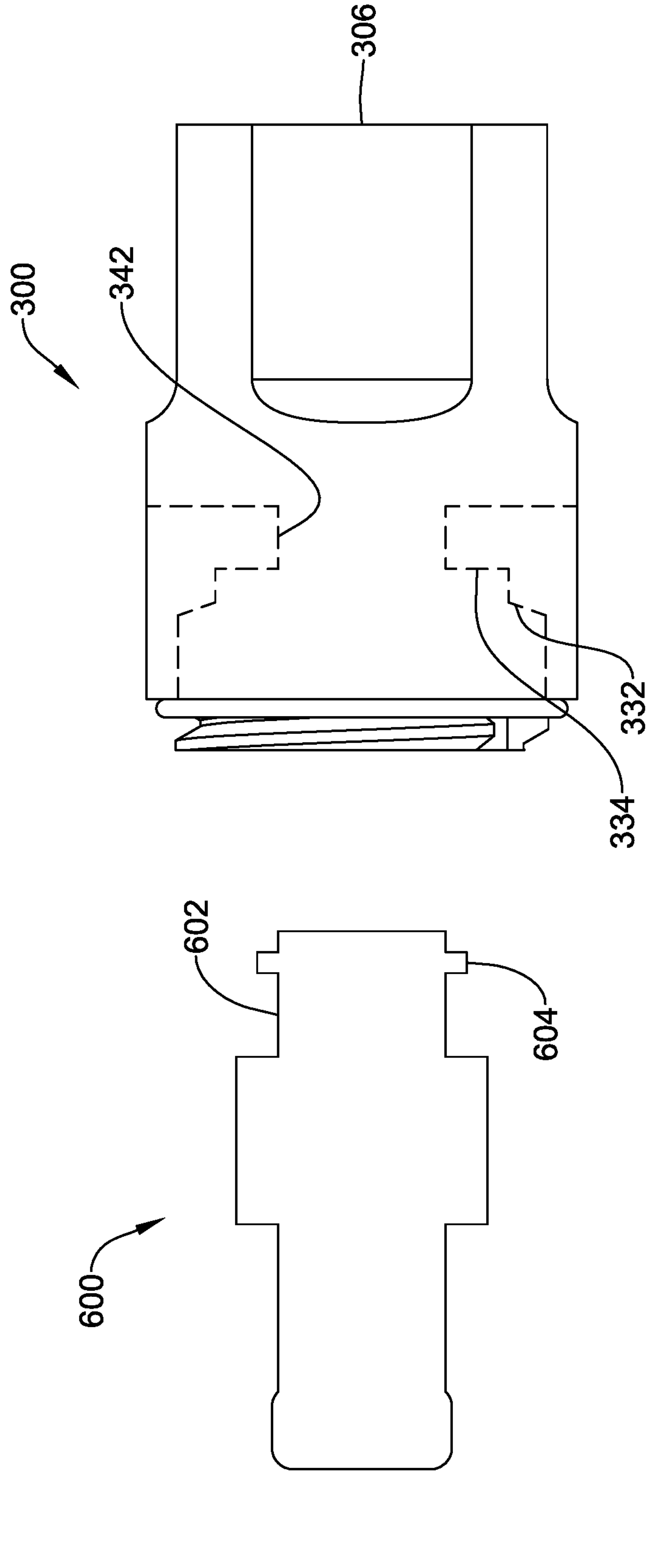
FIG. 9 depicts a side view of the illustrative connector of FIG. 3 with a third receiver of a third type.

FIG. 9 depicts a side view of the illustrative connector 300 with a first receiver 600 of a third type, different from both the first and second receiver types 400, 500. In the illustrated embodiment, the third receiver 600 may generally be an externally threaded receiver. The receiver 600 may have a generally tubular body 602 defining a lumen extending therethrough. One or more external threads 604 may be formed in the outer wall of the tubular body 602. The internal threading 342 of the connector 300 may be configured to engage the external threading 604 of the third receiver 600. It is contemplated that the first portion 312 of the connector 300 may be inserted over the exterior of the body 602 of the third receiver 600. The internal threading 342 of the connector 300 may be engaged with the external threading 604 of the third receiver 600 and the connector 300 rotated to secure the connector 300 to the third receiver 600. The number of rotations required to secure the connector 300 to the third receiver 600 may depend, at least in part, on a thickness of the ledge 334 and/or a number of threads present.

In some cases, an O-ring, gasket, or other sealing member may be provided between the connector 300 and the respective receiver 400, 500, 600. While FIGS. 4, 5, 5A, 6, and 6A illustrate three O-rings 344, 346, 348, in some cases, the connector 300 may only include a single O-ring positioned to provide a seal with a particular receiver 400, 500, 600. For example, an O-ring 344 may be positioned adjacent the first end 310 of the second portion 314 such that when the connector 300 is assembled with the first receiver type 400, the O-ring 344 compresses to provide a fluid tight seal between the components. The O-ring 344 may be sized to have an inner diameter similar in size the first outer diameter D1 of the connector 300, although this is not required. In another example, an O-ring 346 may be provided adjacent to the second ends 328*a*, 328*b* of the first and second helically extending recesses 324*a*, 324*b* such that when the connector 300 is assembled with the second receiver type 500, the O-ring 346 compresses to provide a fluid tight seal between the components. In another example, an O-ring 348 may be provided on the first side 338 of the second ledge 334 adjacent to the through hole 336 such that when the connector 300 is assembled with the third receiver type 600, the O-ring 348 compresses to provide a fluid tight seal between the components.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases “at least one”, “one or more”, and “and/or”, as used herein, are open-ended expressions that are both conjunctive and disjunctive in operation. The term “a” or “an” entity, as used herein, refers to one or more of that entity. As such, the terms “a” (or “an”), “one or more” and “at least one” can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader’s understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term “comprises/comprising” does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms “a”, “an”, “first”, “second”, etc., do not preclude a plurality. Reference signs in the claims are provided merely as a clarifying example and shall not be construed as limiting the scope of the claims in any way.

What is claimed is:

1. A connector arranged and configured to couple a tube set to an endoscope, the connector comprising:

a housing having a tubular body, a first end, a second end, an exterior surface, and an interior surface defining a lumen extending therethrough;

a first coupling mechanism on the exterior surface of the housing and adjacent to the first end of the housing; and a second coupling mechanism extending on the interior surface of the housing from a first end of the second coupling mechanism adjacent to the first end of the housing to a second end of the second coupling mechanism, the second end of the second coupling mechanism positioned between the first end of the housing and the second end of the housing;

wherein the second coupling mechanism is different from the first coupling mechanism.

2. The connector of claim 1, further comprising a third coupling mechanism positioned between the second end of the second coupling mechanism and the second end of the housing, the third coupling mechanism different from the first and the second coupling mechanisms.

3. The connector of claim 2, wherein the third coupling mechanism comprises internal threading extending about an inner surface of the tubular body.

4. The connector of claim 3, wherein the internal threading is formed about an inner surface of a radially inward extending annular ledge.

5. The connector of claim 2, further comprising a sealing member positioned adjacent to the third coupling mechanism.

6. The connector of claim 1, wherein the first coupling mechanism comprises external threading extending about an outer surface of the tubular body.

7. The connector of claim 6, wherein the external threading is discontinuous about a circumference of the tubular body.

8. The connector of claim 1, wherein the first coupling mechanism comprises a first segment and a second segment, the first and second segments each having an arc length of less than 180° and separated by a first cut-out region and a second cut-out region.

9. The connector of claim 8, wherein the first and second segments include threading extending about an outer surface thereof.

10. The connector of claim 1, wherein the second coupling mechanism comprises a first helically extending recess and a second helically extending recess formed in an inner surface of the tubular body, the first and second helically extending recesses spatially separated from one another.

11. The connector of claim 10, wherein each of the first and second helically extending recesses extends less than 180° about an inner circumference of the tubular body.

12. The connector of claim 10, wherein each of the first and second helically extending recesses extends from a first end to a second end.

13. The connector of claim 12, further comprising a mechanical stop positioned adjacent to the second end of each of the first and second helically extending recesses.

14. The connector of claim 1, further comprising a sealing member positioned adjacent to the first coupling mechanism.

15. The connector of claim 1, further comprising a sealing member positioned adjacent to the second coupling mechanism.

* * * * *